United States Patent
Virtanen et al.

(10) Patent No.: US 7,366,558 B2
(45) Date of Patent: Apr. 29, 2008

(54) ELECTRODE FOR OBTAINING A BIOPOTENTIAL SIGNAL

(75) Inventors: Juha Virtanen, Helsinki (FI); Outi Savinen, Helsinki (FI); Magnus Kåll, Helsinki (FI)

(73) Assignee: General Electric Company, Schenectady, NY (US)

( * ) Notice: Subject to any disclaimer, the term of this patent is extended or adjusted under 35 U.S.C. 154(b) by 24 days.

(21) Appl. No.: 11/473,378

(22) Filed: Jun. 22, 2006

(65) Prior Publication Data
US 2007/0010729 A1 Jan. 11, 2007

(30) Foreign Application Priority Data
Jun. 30, 2005 (FI) .................................. 20055366

(51) Int. Cl.
*A61B 5/04* (2006.01)
(52) U.S. Cl. ....................... 600/391; 600/392
(58) Field of Classification Search ................ 600/391, 600/392
See application file for complete search history.

(56) References Cited

U.S. PATENT DOCUMENTS

| 3,805,769 A * | 4/1974 | Sessions ..................... 600/392 |
| 4,126,126 A | 11/1978 | Bare et al. |
| 4,311,152 A | 1/1982 | Modes et al. |
| 4,995,392 A | 2/1991 | Sherwin et al. |
| 5,305,746 A | 4/1994 | Fendrock |
| 5,309,909 A * | 5/1994 | Gadsby et al. .............. 600/386 |
| 5,458,141 A | 10/1995 | Neil |
| 6,434,410 B1 * | 8/2002 | Cordero et al. ............. 600/396 |
| 2002/0019588 A1 | 2/2002 | Marro et al. |

FOREIGN PATENT DOCUMENTS

| EP | 0 377 997 A2 | 7/1990 |
| EP | 0 571 120 A | 11/1993 |
| WO | WO 02/00096 A2 | 1/2002 |

OTHER PUBLICATIONS

European Search Report having a completion date of Oct. 11, 2006.

* cited by examiner

*Primary Examiner*—Lee S. Cohen
(74) *Attorney, Agent, or Firm*—Andrus, Sceales, Starke & Sawall, LLP

(57) ABSTRACT

An electrode for obtaining a biopotential signal from the skin of a subject. The electrode comprises an adhesive element, an electrode body, an electrically conductive electrode pad, a sponge element, soaked with conductive gel, and means for skin abrasion. The means for skin abrasion comprises abrasion elements forming an integrated structure with the electrode pad, the abrasion elements being so dimensioned that the sponge element prevents the abrasion elements from touching the skin when biopotential signals are measured and enables mechanical contact between the skin and the abrasion elements when the electrode pad is pushed towards the skin. The electrode body is made flexible to enable intentional movement of the electrode pad relative to the adhesive element.

14 Claims, 2 Drawing Sheets

Figure 1 (prior art)
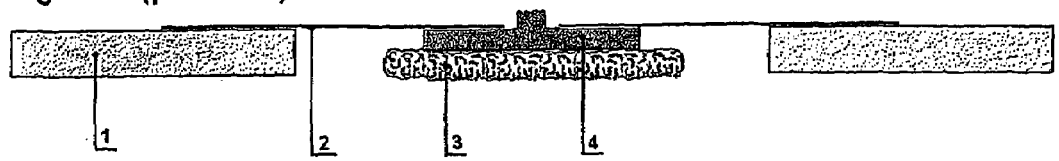
Figure 2
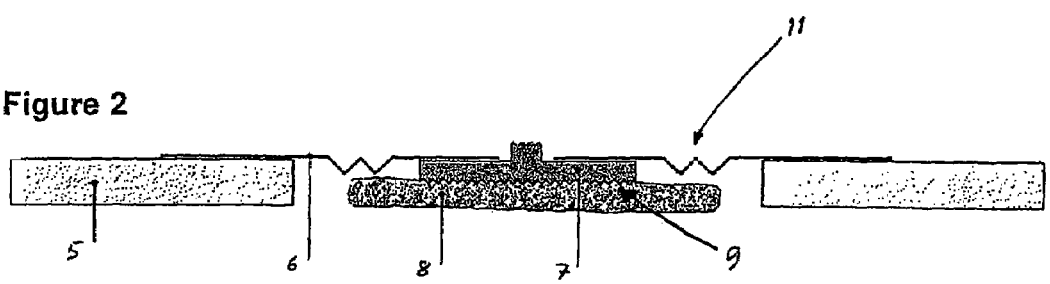
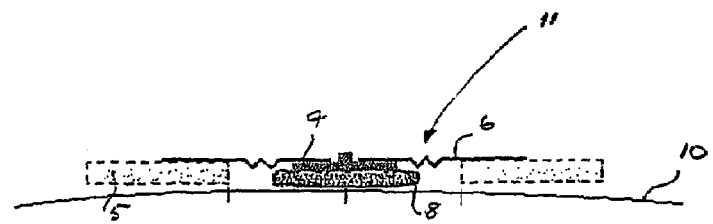
Fig. 3
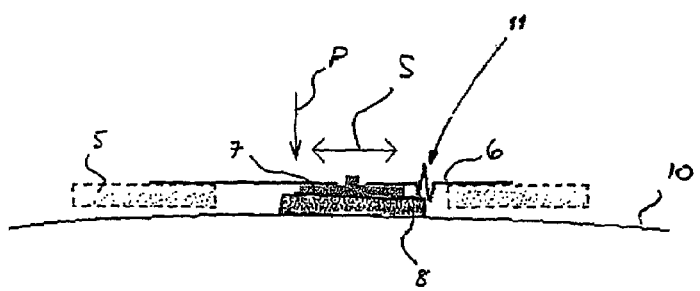
Fig. 4

ELECTRODE FOR OBTAINING A BIOPOTENTIAL SIGNAL

CROSS REFERENCE TO RELATED APPLICATION

The present application claims priority from Finnish Patent Application No. 20055366, filed Jun. 30, 2005.

BACKGROUND OF THE INVENTION

The invention relates to an electrode for obtaining a biopotential signal from the skin of a subject, the electrode comprising an adhesive element, an electrode body, an electrically conducting electrode pad, a sponge element, soaked with conductive gel, and means for skin abrasion.

Diagnostic tests, treatments and the presence of illness require obtaining and monitoring electrical signals generated by the physiological functioning of a patient. Typical electrical signals or biopotentials commonly monitored are those producing electrocardiograms (ECG) from the heart, electroencephalograms (EEG) from the brain and electromyograms (EMG) from muscles. While the duration of most of the biopotential recordings are of the order of one hour, for example intensive care patients may benefit from continuous EEG monitoring longer than 24 hours.

When carrying out for example high-quality surface EEG recordings, skin preparation is necessary for enabling the electrode gel to penetrate through the outer layers of the skin. The electrical bypassing of the outer layers of the skin reduces both the contact noise and the signal artefacts due to the movement of the patient or the electrodes. The most frequently used method for skin preparation is manual abrasion of skin prior attaching the electrodes. This method has two essential shortcomings. First, the user, for example a nurse or a doctor, gets feedback about the quality of skin abrasion only after attaching the electrodes. In case of poor contact, the user has to remove the electrodes in order to repeat the procedure. Secondly the quality of the contact may degrade during long measurement sessions and the only way to refresh it is to remove the electrodes and redo skin preparation.

In prior art self-prepping electrodes, i.e. electrodes having properties for carrying out skin preparation without removing the electrode from skin, have been introduced to overcome the above-mentioned shortcomings.

As an example of the electrodes known in the prior art the electrode described in U.S. Pat. No. 4,126,126 can be mentioned. Said U.S. patent describes a non-metallic pre-gelled electrode with a slightly abrasive lower surface of the gel pad, which continuously performs abrasive function during usage of the electrode, i.e. the operation principle of the electrode is based on passive skin abrasion. The passive skin abrasion based on electrode movement on the skin when the patient moves is effective in stress ECG monitoring, but not with EEG monitoring, in which movements especially in case of sedated patients are minimal.

As another example of the prior art U.S. Pat. No. 5,305,746 can be mentioned. Said U.S. patent describes a disposable, pre-gelled, self prepping electrode. This known electrode is provided with non-conductive flexible tines that penetrate outer layers of the skin without removing any skin, i.e. there is no skin abrasion. This solution provides good contact throughout long recordings, but unfortunately the electrodes feel uncomfortable to the patient during long measurement sessions.

As a third example of the prior art U.S. Pat. No. 4,311,152 can be mentioned. Said U.S. patent describes a medical electrode and a system for minimizing motion artefacts. The patent describes an electrode and a tool for abrading the skin while the electrode is a place, i.e. the solution relates to intermittent skin abrasion. In this case the electrode comprises a conductive member and an abrasive member, which can be rotated with respect to the skin. Also other types of movements are mentioned in the patent. This method is effective, but as also with the electrode described in U.S. Pat. No. 4,126,126, the abrasive pad against the skin tends to irritate it especially if the recording time is several hours long.

SUMMARY OF THE INVENTION

The object of the present invention is to obtain an electrode by which the disadvantages of the prior art can be eliminated. This is obtained with the present invention. The present invention is characterized in that the means for skin abrasion comprises abrasion elements forming an integrated structure with the electrode pad, the abrasion elements being so dimensioned that the sponge element prevents the abrasion elements from touching the skin when biopotential signals are measured and enables mechanical contact between the skin and the abrasion elements when the electrode pad is pushed towards the skin, and that the electrode body is made flexible to enable intentional movement of the electrode pad relative to the adhesive element.

The advantage of the invention is that the invention is simple and very practical in use. Simple construction leads to low costs and practicality leads to good results in use. The electrode of the invention is also very comfortable to the patient especially in long-term recordings. The electrode is also very versatile, i.e. the electrode can be used in all surface biopotential measurements.

BRIEF DESCRIPTION OF THE DRAWINGS

In the following the invention will be described in greater detail by means of examples illustrated in the attached drawing, in which FIG. 1 shows an example of the electrodes known in the prior art, FIG. 2 shows an example of the electrode of the present invention, FIG. 3 shows the electrode shown in FIG. 2 attached to the skin, FIG. 4 shows the electrode shown in FIG. 3 during abrasion step

DETAILED DESCRIPTION OF THE INVENTION

Figure 5:
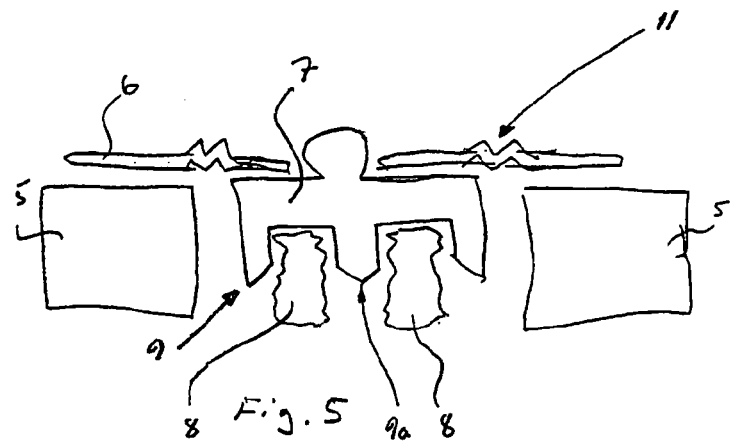
FIG. 5 shows another example of the present invention.

FIG. 1 shows a typical example of the prior art. The electrode consists of an adhesive element, i.e. an adhesive foam tape 1, electrode body 2 made of shaped plastic film, abrasive harsh sponge 3 soaked with conductive gel, and an electrode pad 4. The abrasive sponge 3 functions as a preparation instrument and a gel carrier. Movement of the electrode part and the abrasive sponge relative to the skin surface performs the preparation. A coarse sponge 3 rasps the skin surface and makes the abrasion. An abrasive sponge can be manufactured of e.g. stiff cellular plastic. The elements described above are advantageously circular elements.

In the electrode of the prior art described above the sponge 3, i.e. the abrasive element, is always in contact with the skin when the electrode is attached to the skin. This leads to the disadvantages described earlier in the text.

FIG. 2 shows one embodiment of the invention. Reference number 5 shows an adhesive element, which can be for example an adhesive foam tape. Reference number 6 shows an electrode body. The electrode body can be made of appropriate plastic film. Reference number 7 shows an electrically conductive electrode pad. Reference number 8 shows a soft, pre-gelled sponge element. The electrode pad may be made of a conductive material or made of a non-conductive material and provided with a coating of a conductive material.

According to the basic idea of the invention the electrode pad 7 is provided with means for intermittent skin abrasion. The means for intermittent skin abrasion comprises abrasion elements 9 forming an integrated structure with the electrode pad. The abrasion elements 9 are so dimensioned that the sponge element 8 prevents the abrasion elements 9 from touching the skin when bioelectric signals are measured and enables the mechanical contact between the skin and the abrasion elements 9 when the electrode pad 7 is pushed towards the skin. The electrode body 6 is made flexible to enable intentional movement of the electrode pad 7 relative to the adhesive element 5. The abrasion elements are rigid enough so that no substantial bending takes place during lateral movement of the electrode pad.

The basic idea of the invention described above can be seen very clearly from FIGS. 3 and 4. Reference number 10 shows the skin in FIGS. 3 and 4.

In the embodiment of FIGS. 2-4 the abrasion elements 9 are provided on the bottom surface of the electrode pad 7. The abrasion elements 9 are arranged to form an integrated structure with the electrode pad 7. The abrasion elements 9 can be formed for example by machining the bottom surface of the electrode pad appropriately or the abrasive elements can be formed as a separate structure, which can be fastened to the bottom surface of the electrode pad. The whole bottom surface of the electrode pad can be covered with the abrasion elements. This is not however the only alternative but the abrasion elements 9 can also cover only a part or several parts of the bottom surface of the electrode pad 7. The abrasion elements 9 can be formed of toothing having teeth advantageously several millimetres high. Minimum height of the teeth is roughly of the order of 0,5 mm. The height of the abrasion elements, e.g. the teeth must be less than the thickness of the sponge element in its free condition, i.e. when the electrode pad is attached to the skin but not pushed towards the skin. The thickness of the sponge element may be more than the length of the teeth so that the teeth are not in contact with the skin when the electrode is attached to the skin and is laying freely on the skin without any pushing of the electrode pad. This embodiment is shown in the Figures. This is however not the only possible embodiment. Within the spirit of the invention it is also quite possible to use a relatively thin sponge and provide a spring element between the sponge element and the electrode pad. Said sponge and said spring element form together the sponge element acting in the same way as described above in connection with a relatively thick sponge element, i.e. the sponge element prevents the abrasion elements from touching the skin when the electrode is attached to the skin and when the electrode pad is not pushed towards the skin. Said spring element can be any appropriate element, for example a coil spring or springs, a plate spring or springs, or a combination thereof, a pneumatic element, air cushion element etc.

In the embodiment of FIGS. 2-4 the abrasion elements 9 penetrate through the sponge element 8 into contact with skin 10 when the electrode pad 7 is pushed towards the skin. Said pushing movement is shown by arrow P in FIG. 4. The electrode pad 7 is moved sideways relative to the adhesive element 5 when abrasion step is carried out. In said abrasion step the abrasion elements are in contact with skin. Said sideways directing movement is shown by arrow S in FIG. 4. As shown in FIG. 4 the electrode pad moves relative to the adhesive element 5 when said abrasion step is carried out. Said relative movement is obtained by special properties, i.e. flexibility properties of the electrode body 6. Said flexibility properties can be obtained for example by elasticity of the electrode body 6 material. It is also possible to use accordion folds 11 to obtain the propertied desired. Said accordion folds are used in the embodiment of FIGS. 2-4.

Figures 6, 7:
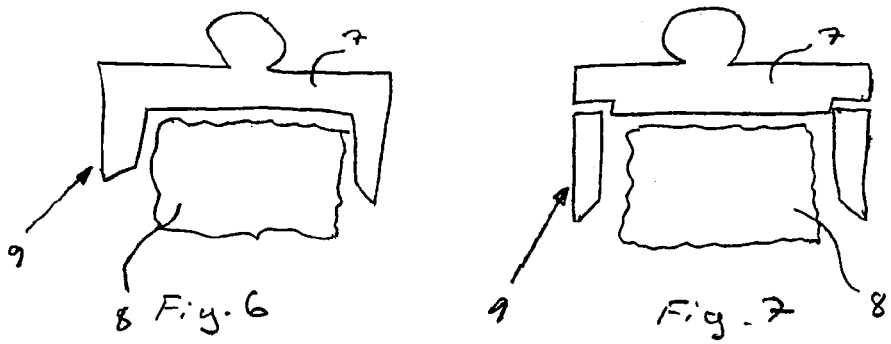
FIG. 6 shows a modification of the example shown in FIG. 5.
FIG. 7 shows a modification of the construction shown in FIG. 6.
Figure 9:
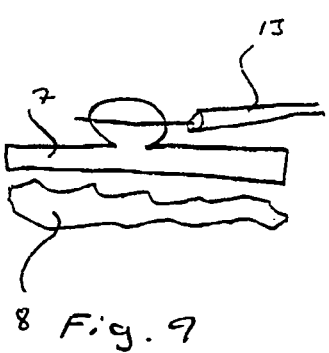
FIG. 9 shows an advantageous detail for use in connection with the invention.

The embodiment shown in FIGS. 2-4 is however not the only possible one. Within the spirit of the invention it is also quite possible to create a structure in which the abrasion elements 9 do not penetrate through the sponge element 8 but move beside the sponge element into contact with skin 10. This embodiment is shown in FIG. 5. FIG. 5 uses same reference numbers as used in corresponding details in FIGS. 2-4. This embodiment uses one or more knife-elements placed at the outer edge of the electrode pad 7 as abrasion elements 9. Said knife-element can for example extend around the electrode pad. It is also possible to use a saw-formed abrasion edge in connection with said knife-element. The embodiment of FIG. 5 comprises also an abrasion element 9a placed at the middle area of the bottom surface of the electrode pad 7. Said centrally placed abrasion element 9a can be for example a pin-like element or a knife-like element. It is however quite possible to materialize the construction without said centrally placed abrasion element 9a as shown in FIG. 6. FIG. 9 shows only the electrode pad 7 and the sponge element 8, otherwise the construction can be similar to the construction shown in FIG. 5.

The edges of the knife elements and the point of eventual pin of said pin-like element as well as the points of the teeth shown in FIGS. 2-4 need not be very sharp. This is due to the fact that only gentle abrasion is needed not excessive painful abrasion.

The operation principle of the embodiments shown in FIGS. 5 and 6 is identical to the operation of the embodiment shown in FIGS. 2-4, i.e. the principle shown in FIGS. 3 and 4 can be adapted to the embodiments shown in FIGS. 5 and 6.

The abrasion elements can be made of electrically conducting material or electrically non-conductive material as told before. Abrasion elements 9 made of electrically conducting material are shown in FIGS. 2-4 and 5 and 6. FIG. 7 shows an embodiment in which the abrasion elements 9 are made of non-conducting material, i.e. the element or elements forming the abrasion element 9 made of non-conducting material are fastened to the conductive electrode pad. Said fastening can be made for example by adhesion, press fits etc. The electrode pad can be made of conducting material, for example ABS-plastic blended with carbon fibres or sintered Ag/AgCl. Said conductive material can also be metal, for example silver and it may have a cover layer of e.g. silver chloride. The electrode material can also be non-conductive plastic, which is covered with conductive material, for example silver or silver chloride. The requirements for the conducting properties of the electrode pad depend on the application. In EEG recordings typical target value is from 0 to 1 kohm, impedances about 10 kohm being not well suited for the application. For ECG and EMG the typical target values are also from 0 to 1 kohm, but for these measurements the upper limit is of the order of 100 kohm. Said non-conductive material can be for example any appropriate plastic material.

Figure 8:
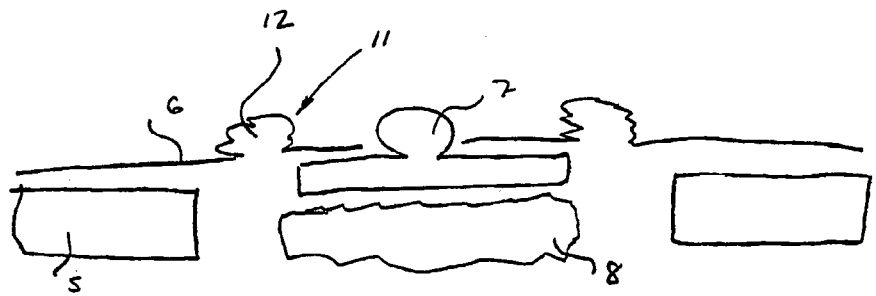
FIG. 8 shows a third example of the invention.

FIG. 8 shows the third embodiment of the invention. FIG. 8 uses the same reference numbers as used in corresponding details shown in FIGS. 2-7. In this embodiment the accordion folds 11 are formed so that there is also an expansion chamber 12 for gel. Said expansion chamber 12 is advantageous because in some embodiments there must be room for gel flowing away from the sponge element 5 when the electrode pad 7 is pushed towards the skin during abrasion step as discussed above. In some embodiments the air-filled cavity between the foam tape 5 and the electrode pad 7 provides sufficient expansion chamber functionality.

In long-term recordings it is advantageous that there are no air-filled cavities against the skin. Hence, in some applications it may be advantageous that the diameter of the sponge element 8 is substantially the same as the inner diameter of the adhesive element 5 Similarly, in embodiments shown in FIGS. 5, 6 and 7 it may be advantageous to have an additional ring-shaped sponge element (not shown in the Figures) in between the adhesive element 5 and the abrasive elements 9.

Figure 10:
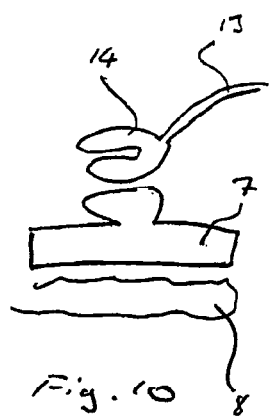
FIG. 10 shows another advantageous detail for use in connection with the invention.

FIGS. 9 and 10 show alternative constructions how electrical cables 13 can be connected to the electrode pads 7. In the invention it is advantageous that flexible cable 13 is used. This is because flexible cable enables effective abrasion movement of the electrode pad 7. Furthermore, flexible cable makes the electrode system less prone to motion artefacts, because the mechanical forces transmitted to the electrode pad via the cable are minimised. Cable 13 can be connected directly to the electrode pad 7 as shown in FIG. 9, for example by connecting the cable to an appropriate connecting surface or device arranged in the electrode pad, or an appropriate cable end 14 can be used as shown in FIG. 10.

The embodiments described above are not intended to restrict the invention in any way, but the invention may be modified completely freely within the scope of the claims. Therefore, it is obvious that the electrode of the invention or the details of the electrode do not necessarily have to be exactly the same as shown in the Figures, but other solutions are possible, too.

The invention claimed is:

1. An electrode for obtaining a bioelectric signal from the skin of a subject, the electrode comprising:
   an adhesive element having a bottom surface for attaching the electrode to the skin;
   an electrode body coupled to the adhesive element;
   an electrically conductive electrode pad coupled to the electrode body;
   a sponge element soaked with conductive gel and coupled to a bottom surface of the electrode pad; and
   abrasion elements integrated with the electrode pad and extending towards the skin when the adhesive element is attached to the skin;
   the abrasion elements being so dimensioned that the sponge element
      prevents the abrasion elements from touching the skin when the adhesive element is attached to the skin, and
      enables mechanical contact between the skin and the abrasion elements when the electrode pad is moved in a direction towards the skin;
   the electrode body being flexible enough to enable movement of the electrode pad in the direction towards the skin and to also enable movement in a direction horizontal to the skin.

2. The electrode of claim 1, wherein the abrasion elements comprise toothing provided on the bottom surface to the electrode pad.

3. The electrode of claim 1, wherein the abrasion elements comprise multiple knife-elements placed at an outer edge of the electrode pad.

4. The electrode of claim 3, wherein the abrasion elements comprise an abrasive element placed at a middle area of the bottom surface of the electrode pad.

5. The electrode of claim 1, wherein the abrasion elements comprise a circular knife-element placed at an outer edge of the electrode pad.

6. The electrode of claim 1, wherein the abrasion elements are formed of electrically conducting material.

7. The electrode of claim 1, wherein the abrasion elements are formed of electrically non-conductive material.

8. The electrode of claim 1, wherein the abrasion elements are arranged to contact the skin of the subject through the sponge element.

9. The electrode of claim 1, wherein the abrasion elements are arranged to contact the skin of the subject beside the sponge element.

10. The electrode of claim 1, wherein the flexibility of the electrode body is obtained by elasticity of the electrode body material.

11. The electrode of claim 1, wherein the flexibility of the electrode body is obtained by accordion folds made into the electrode body material.

12. The electrode of claim 1, wherein the abrasion elements are substantially rigid elements.

13. The electrode of claim 1, wherein the diameter of the sponge element is substantially the same as an inner diameter of the adhesive element.

14. An electrode for obtaining a bioelectric signal from the skin of a subject, the electrode comprising:
   an adhesive element having a bottom surface for attaching the electrode to the skin;
   an electrode body coupled to the adhesive element;
   an electrically conductive electrode pad coupled to the electrode body;
   a sponge element soaked with conductive gel and coupled to a bottom surface of the electrode pad; and
   abrasion elements integrated with the electrode pad and extending towards the skin when the adhesive element is attached to the skin;
   the abrasion elements being so dimensioned that the sponge element
      prevents the abrasion elements from touching the skin when the adhesive element is attached to the skin, and
      enables mechanical contact between the skin and the abrasion elements when the electrode pad is moved along a direction towards the skin;
   the electrode body being flexible enough to enable movement of the electrode pad relative to the adhesive element;
   wherein the abrasion elements comprise a circular knife-element placed at an outer edge of the electrode pad.

* * * * *